US00PP31766P2

(12) United States Plant Patent
Sapia

(10) Patent No.: US PP31,766 P2
(45) Date of Patent: May 12, 2020

(54) ***SALVIA* PLANT NAMED 'HYBSV18020'**

(50) Latin Name: ***Salvia buchananii* x *Salvia splendens***
Varietal Denomination: HYBSV18020

(71) Applicant: Flavio Sapia, Sanremo (IT)

(72) Inventor: Flavio Sapia, Sanremo (IT)

( * ) Notice: Subject to any disclaimer, the term of this patent is extended or adjusted under 35 U.S.C. 154(b) by 0 days.

(21) Appl. No.: 16/501,890

(22) Filed: Jun. 27, 2019

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — Barbara Campbell; Cochran Freund & Young LLC

(57) ABSTRACT

A new *Salvia* plant particularly distinguished by a plant having orange-red flowers, and an upright plant habit, is disclosed.

1 Drawing Sheet

Genus and species: *Salvia buchananii* x *Salvia splendens*.
Variety denomination: 'HYBSV18020'.

BACKGROUND OF THE NEW PLANT

The present invention comprises a new and distinct variety of *Salvia*, botanically known as *Salvia buchananii* x *Salvia splendens*, and hereinafter referred to by the variety name 'HYBSV18020'. 'HYBSV18020' as a branch mutation from the parent line SALMIA 'Dark Purple' (unpatented) in April 2015 in Sanremo, Italy.

In May 2015 in Juja, Kenya, 'HYBSV18020' was first vegetatively propagated by stem cuttings. 'HYBSV18020' was found to reproduce true to type in successive generations of asexual propagation via stem cuttings.

SUMMARY

The following are the most outstanding and distinguishing characteristics of this new variety when grown under normal horticultural practices in Sanremo, Italy and Stuttgart, Germany.

1. A plant having orange-red flowers; and
2. An upright plant habit.

DESCRIPTION OF THE PHOTOGRAPH

This new *Salvia* plant is illustrated by the accompanying photograph which shows the plant's overall plant habit including form, flowers, and foliage. The photograph is of a 7-month-old plant grown in a pot outdoors in Stuttgart, Germany in September 2018. The colors shown are as true as can be reasonably obtained by conventional photographic procedures.

DESCRIPTION OF THE NEW VARIETY

The following detailed descriptions set forth the distinctive characteristics of 'HYBSV18020'. The data which define these characteristics were collected from in Stuttgart, Germany in May 2019 on 11-week-old plants grown in a 12 cm pot in a glass greenhouse, pinched twice with added plant growth regulator. Color references are to The R.H.S. Colour Chart of The Royal Horticultural Society of London (R.H.S.), 5$^{th}$ edition (2007).

Classification:
- *Family*.—Lamiaceae.
- *Botanical*.—*Salvia buchananii* x *Salvia splendens*.
- *Common*.—Sage.
- *Designation*.—'HYBSV18020'.

Parentage:
- *Mutation parent*.—SALMIA 'Dark Purple' (unpatented).

Plant:
- *Plant and growth habit*.—Upright.
- *Plant height*.—55 cm to 60 cm.
- *Plant diameter*.—55 cm to 65 cm.
- *Type*.—Vegetative stem cuttings.
- *Time to produce a rooted young plant*.—3 weeks.
- *Root description*.—White to light brown RHS 158C to RHS 166C, fine, freely branching and dense.

Stems (main branch):
- *Length*.—About 1.0 cm to 1.5cm; the main stem was pinched after 1.5 cm.
- *Width*.—0.6 cm to 0.7 cm.
- *Color*.—RHS 183C.
- *Shape*.—Round.
- *Texture*.—Glabrous.

Branches (lateral stems):
- *Quantity per plant*.—4.
- *Length (to base of raceme)*.—50 cm to 55 cm.
- *Width/diameter of one branch*.—0.6 cm.
- *Internode length*.—5 cm at the base.
- *Color*.—RHS 137C.
- *Shape*.—Round at the base, rectangular in younger parts.
- *Texture*.—Glabrous.

Leaves:
- *Arrangement*.—Opposite.
- *Attachment*.—Petiolate.
- *Quantity per branch*.—3 to 4.

*Shape*.—Ovate.
*Apex*.—Obtuse.
*Base*.—Acute.
*Margin*.—Crenate.
*Thickness of leaves*.—0.2 mm to 0.3 mm.
*Length*.—5 cm to 7 cm.
*Width*.—3.3 cm to 4.5 cm.
*Venation pattern*.—Pinnate for the primary vein; craspedodromous for the secondary veins.
*Vein description, upper surface*.—Raised, RHS 185C; depressed, RES 138C.
*Vein description, lower surface*.—Raised, RHS 185C.
*Texture* (*both surfaces*).—Glabrous.
*Color*.—Upper surface: RHS 139A. Lower surface: RHS 137C.
*Fragrance*.—Chlorophyll-like.
*Stipules*.—Absent.
*Petiole*.—Shape: Round at the lower side, flat with a depressed vein on the upper surface. Length: 2.5 cm to 3.5 cm. Diameter: 0.15 cm.
*Texture* (*both upper and lower surfaces*).—Glabrous.
*Color*.—Upper surface: RHS 139A. Lower surface: RHS 148B with some anthocyanin, RHS 180A.

Flower:
*Flower type*.—Raceme.
*Natural flowering season*.—Spring and summer.
*Flower longevity on the plant*.—5 to 7 days.
*Shape*.—Bell-shaped, zygomorphic.
*Fragrance*.—Sweet to lemon-like.
*Diameter*.—0.3 cm to 0.8 cm.
*Length*.—5 cm.
*Arrangement*.—Flowers are arranged in whorls.
*Number of flowers per whorl and per raceme*.—6 per whorl, 75 to 90 per raceme.
*Distance between whorls*.—1.5 cm to 2.8 cm.
*Bud*.—Shape: Torpedo-like. Length: 1.8 cm. Width: 0.4 cm. Texture: Ciliate. Color: RHS 46B.
*Corolla*.—Shape: Tubular. Length: 5 cm. Width: 0.7 cm. Texture: Ciliate. Color (both surfaces): RHS 47A.
*Petals*.—Quantity: 1 tube (consists of 5 petals fused in a base to form a tube). Upper petal: Quantity of upper petals per flower: 1 (2 fused petals). Aspect: Dropping. Shape: Cylindrical. Length: 4.8 cm to 5.5 cm. Width: 0.5 cm. Texture: Upper surface: Ciliate. Lower surface: Glabrous. Apex: Cylindrical-obtuse. Base: Fused. Margin: Entire. Color: Upper surface: RHS 42A. Lower surface: RHS 41C. Lower petal, lip: Quantity of lower petals per flower: 1 (3 fused petals). Aspect: Dropping. Shape: Cylindrical. Length: 4.3 cm to 4.6 cm. Width: 0.8 cm. Texture: Upper surface: Ciliate. Lower surface: Glabrous. Apex: Marginate, 0.1 cm to 0.2 cm for depth of notch. Base: Cylindrical. Margin: Entire. Color: Upper surface: RHS 41A. Lower surface: RHS 41D. Floral Bracts: Absent. Calyx: Shape: Cup-like. Length: 2 cm. Width: 0.9 cm at the tip, 0.4 cm at the base. Sepals: Luster: Absent. Arrangement: Adnate, calyx tube. Number per flower: 1 (2 adnate). Length: 2 cm. Width: 0.7 cm at the base and 2.2 cm at the tip. Shape: Lanceolate. Apex: Acuminate. Base: Cuneate. Margin: Ciliate. Texture (both upper and lower surfaces): Glabrous. Color: Upper surface: RHS 145C at the base, RHS 146C in the middle, and RHS 46A at the tip. Lower surface: RHS 145C at the base, RHS 146C in the middle, and RHS 46A at the tip.
*Peduncles*.—Length (to first flower whorl): 20 cm to 25 cm. Length (to uppermost flower whorl): 45 cm to 50 cm. Shape: Round at the base, rectangular in younger parts. Diameter: 0.3 cm. Texture: Glabrous. Color: RHS 137C.
*Pedicel*.—Length: 0.6 cm to 0.7 cm. Width: 1 mm. Texture: Pubescent. Color: RHS 34B.

Reproductive organs:
*Stamens*.—Quantity per flower: 2. Filament length: 1.4 cm to 1.7 cm. Filament color: RHS 157D. Anther shape: Elliptic. Anther length: 0.3 mm to 0.4 mm. Anther width: 0.1 cm. Anther color: RHS 46A. Pollen amount: Absent.
*Pistils*.—Quantity per flower: 1. Pistil length: 5 cm to 5.5 cm. Stigma shape: Filamentous. Stigma length: 0.3 cm. Stigma width: 0.03 cm. Stigma color: RHS 41D. Style length: 5 cm. Style color: RHS 41D at the end, and RHS 155D for the rest of the style. Ovary color: RHS 8D. Ovary length: 0.3 cm. Ovary width: 0.2 cm.

Fruit and seed set: None observed.
Disease and pest/insect resistance: No disease and pest/insect resistance observed.

COMPARISON WITH PARENTAL LINE AND KNOWN VARIETY

'HYBSV18020' is distinguished from mutation parent as described in Table 1.

TABLE 1

Comparison with Mutation Parent

| Characteristic | 'HYBSV18020' | Mutation Parent SALMIA 'Dark Purple' |
|---|---|---|
| Color | Orange-red | Dark purple |

'HYBSV18020' is most similar to the *Salvia* 'Wendy's Wish' (U.S. Plant Pat. No. 21,889). Differences between the varieties are described in Table 2.

TABLE 2

Comparison with Similar Variety

| Characteristic | 'HYBSV18020' | 'Wendy's Wish' |
|---|---|---|
| Color | Orange-red | Purple |

I claim:
1. A new and distinct variety of *Salvia* plant designated 'HYBSV18020' as illustrated and described herein.

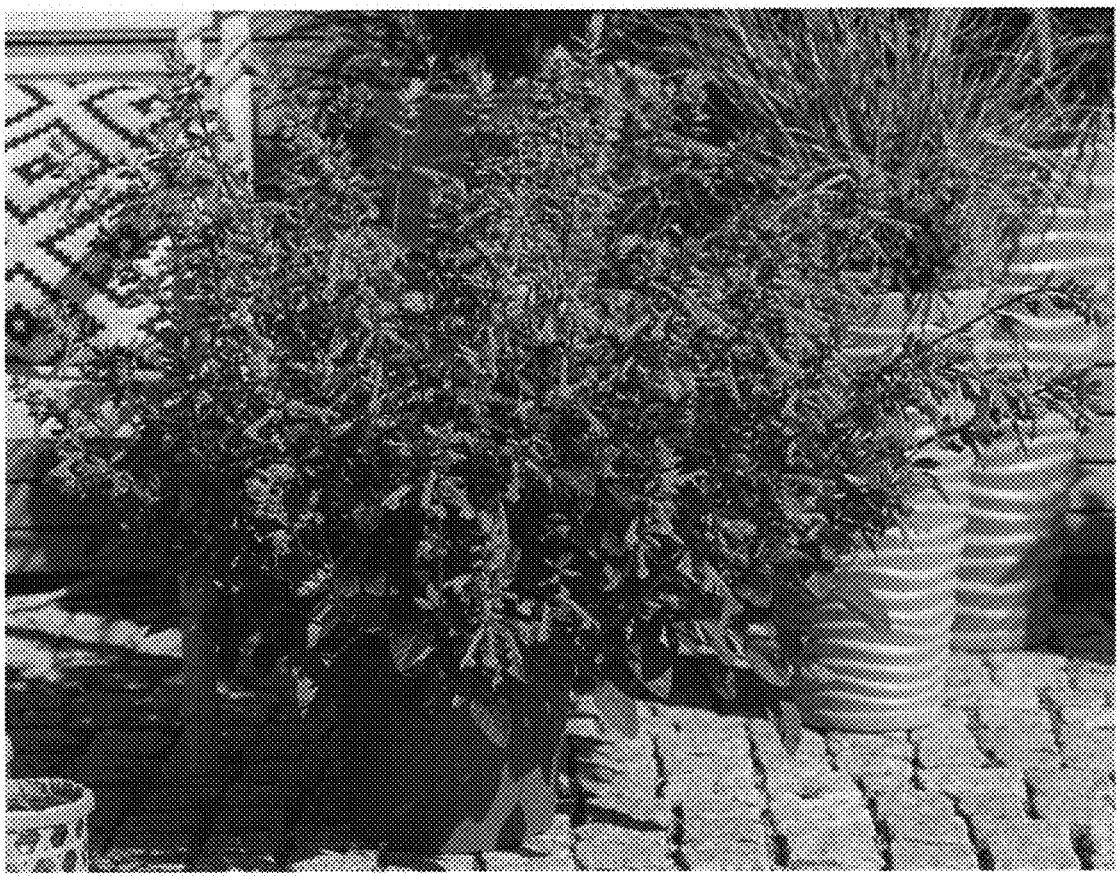

* * * * *